US00PP32768P2

(12) United States Plant Patent
Vail

(10) Patent No.: US PP32,768 P2
(45) Date of Patent: Jan. 26, 2021

(54) ***MANGIFERA* PLANT NAMED 'ORANGE STAR'**

(50) Latin Name: *Mangifera indica*
Varietal Denomination: Orange Star

(71) Applicant: Ross Vail, El Pescadero (MX)

(72) Inventor: Ross Vail, El Pescadero (MX)

( * ) Notice: Subject to any disclaimer, the term of this patent is extended or adjusted under 35 U.S.C. 154(b) by 0 days.

(21) Appl. No.: 16/602,748

(22) Filed: Dec. 3, 2019

(51) Int. Cl.
*A01H 5/08* (2018.01)
*A01H 6/00* (2018.01)

(52) U.S. Cl.
USPC ..... Plt./159

(58) Field of Classification Search
USPC ..... Plt./159
See application file for complete search history.

*Primary Examiner* — Susan McCormick Ewoldt
(74) *Attorney, Agent, or Firm* — Cassandra Bright

(57) ABSTRACT

A new and distinct cultivar of *Mangifera* plant named 'Orange Star' is disclosed, characterized by a unique flavor which includes a citrus component. Fruit lacks a long fiber and has a firmness at maturity which eases processing and cubing. Fruit flesh is orange, trees are observed disease resistant. The new variety is a *Mangifera*, suitable for the production of fruit.

2 Drawing Sheets

Figure 1:
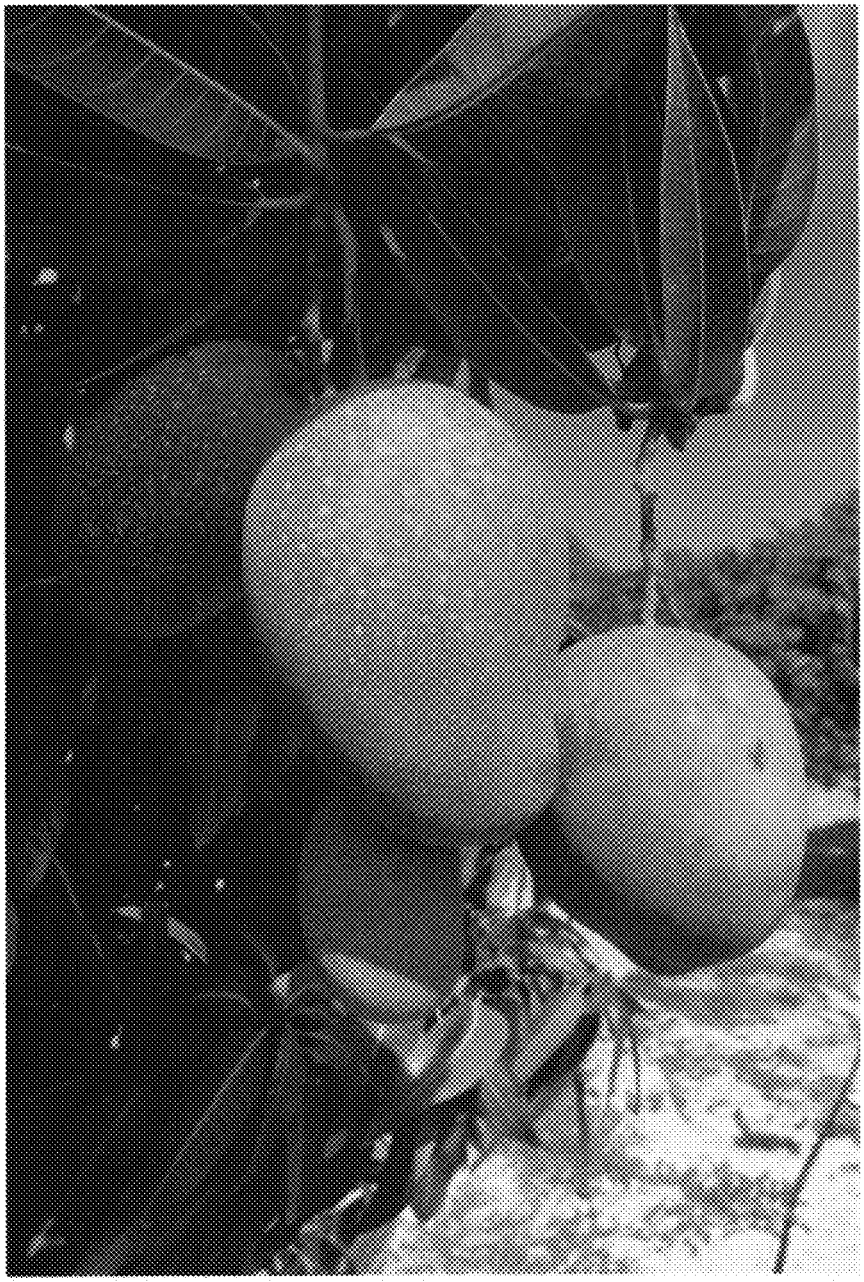

Latin name of the genus and species: *Mangifera indica.*
Variety denomination: 'Orange Star'.

BACKGROUND OF THE INVENTION

The new *Mangifera* cultivar is a product of a planned breeding program conducted by the inventor, in La Paz, Mexico. The objective of the breeding program was to produce new *Mangifera indica* varieties with improved fruit for commercial production. The cross resulting in this new variety occurred during 1999.

The seed parent is the unpatented *Mangifera indica* 'Keitt' . The pollen parent is the unpatented *Mangifera indica* 'Lemon Mango'. The new variety resulted from seed planted in 1999. The inventor observed the seedlings during several seasons, and made a final selection of 'Orange Star' at a commercial nursery in La Paz, Mexico Asexual reproduction of the new cultivar was performed by grafting vegetative cuttings onto unpatented *Mangifera indica* rootstock. This was first performed at a commercial nursery in La Paz, Mexico during 2003 and has shown that the unique features of this cultivar are stable and reproduced true to type in successive generations.

SUMMARY OF THE INVENTION

The cultivar 'Orange Star' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Orange Star' These characteristics in combination distinguish 'Orange Star' as a new and distinct *Mangifera* cultivar:

1. Citrus flavor component blends with mango flavor.
2. Lack of long fiber.
3. Firmness of the flesh at maturity for ease of cubing or processing 4. Intense orange color of the flesh.
5. Disease resistant.

PARENTAL COMPARISON

Plants of the new cultivar 'Orange Star' are similar to plants of the seed parent variety in most horticultural characteristics, however, plants of the new cultivar 'Orange Star' differ in the following;

1. Fruit of the new variety ripens more evenly than fruit of 'Keitt'.
2. The new variety produces fruit over a longer period of time than the seed parent, which produces fruit for a small window.
3. The new variety begins fruiting earlier than 'Keitt'.
4. Fruit of the new variety is easier to process, with less waste as the end of the fruit is more uniform.
5. Skin of the new variety is orange, skin of 'Keitt' is green.

Plants of the new cultivar 'Orange Star' are similar to plants of the pollen parent variety in most horticultural characteristics, however, plants of the new cultivar 'Orange Star' differ in the following;

1. Trees of the new variety produce more lateral branches, compared to the pollen parent which grows straight up.
2. Trees of the new variety grow faster during the early years of planting than trees of the pollen parent.
3. Trees of the new variety are less susceptible to powdery mildew and typical pests of *Magnifera* than the pollen parent.
4. Fruit of the new variety is not as susceptible to bacterial black spot.
5. Fruit of the new variety is orange, fruit of the pollen parent is yellow.
6. Fruit of the new variety is larger.
7. Fruit shape of the new variety is broader, less elongated than fruit of the pollen parent.

COMMERCIAL COMPARISON

Plants of the new cultivar 'Orange Star' are comparable to the variety *Mangifera* 'Kent', unpatented. The two *Man-*

*gifera indica* varieties are similar in most horticultural characteristics; however, plants of the new variety 'Orange Star' differ in the following characteristics:

1. Fruit of the new variety does not wrinkle when ripe, as observed in fruit of 'Kent'.
2. Fruit of the new variety does not produce white spots on the skin when ripe, as observed in fruit of 'Kent'.
3. Fruit of the new variety has a longer shelf life than fruit of 'Kent'.
4. Skin color of fruit of the new variety is orange, whereas skin color of fruit of the variety 'Kent' is green with some blush.
5. Trees of the new variety are less susceptible to anthracnose than 'Kent'.
6. Fruit quality is less variable under variable weather conditions than 'Kent'.

Plants of the new cultivar 'Orange Star' are comparable to the variety *Mangifera* 'Haden', unpatented. The two *Mangifera indica* varieties are similar in most horticultural characteristics; however, plants of the new variety 'Orange Star' differ in the following characteristics:

1. Young trees of the new variety are less susceptible to cold damage than those of 'Haden'.
2. The new variety reliably produces a fruiting crop more reliably than 'Haden'.
3. Fruit of the new variety is not susceptible to internal breakdown, commercially referred to as "jelly seed", as observed in fruit of 'Haden'.
4. The variety 'Haden' is known to have significant susceptibility to fungal diseases. The new variety is significantly more tolerant of fungal diseases than 'Haden'.

BRIEF DESCRIPTION OF THE PHOTOGRAPHS

The accompanying photograph in FIG. 1 illustrates in full color ripe fruit produced by trees of 'Orange Star' hanging on the tree.

Figure 2:
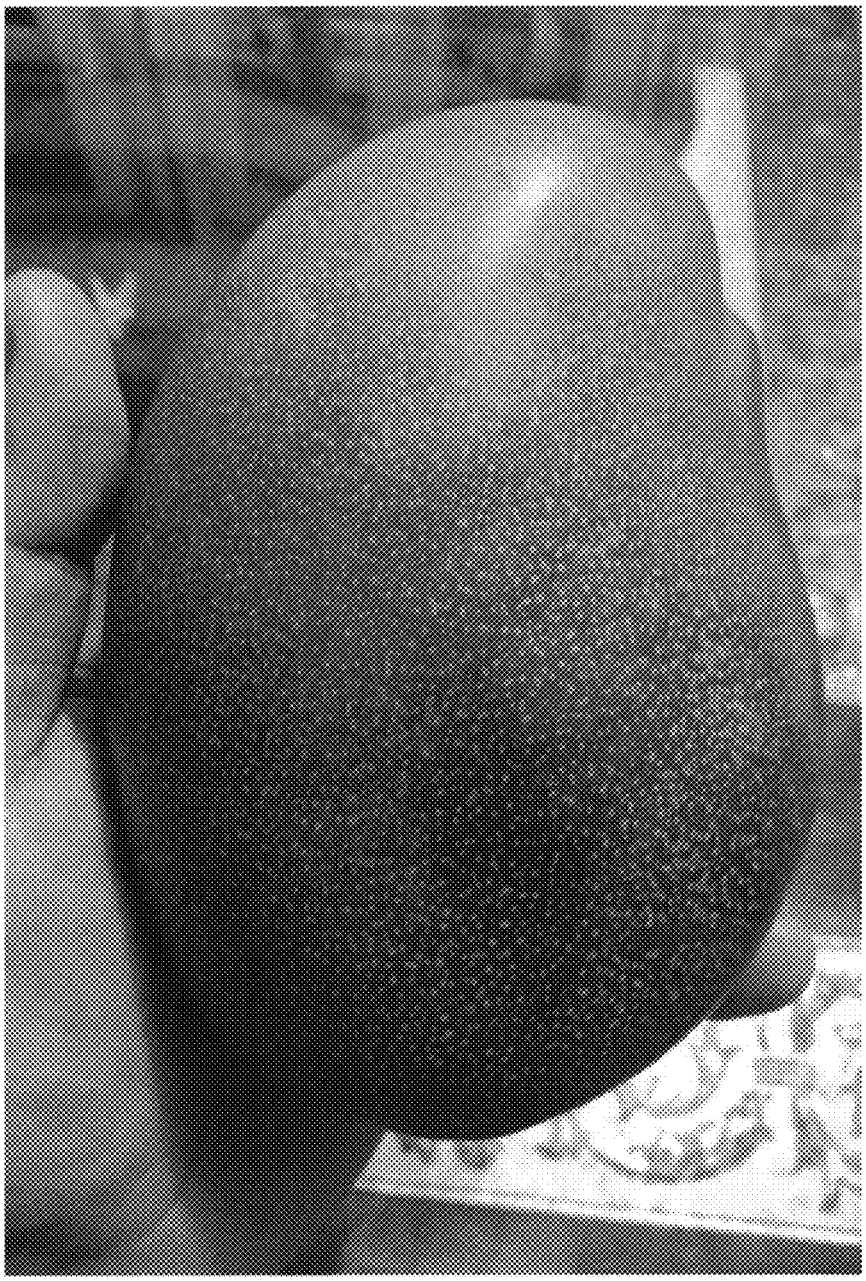

FIG. 2 illustrates in full color a single fruit, depicting the typical shape of fruit produced by trees of 'Orange Star'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Orange Star' plants grown outdoors in La Paz, Mexico. Measurements and numerical values represent averages of typical plant types.

During April through October high temperatures reached between 32 and 38° C. Low temperature during this time was between 15 to 21° C. Between November and March, high temperatures were between 23 to 29° C. Low temperatures were between 12 and 16° C.

Botanical classification: *Mangifera indica* 'Orange Star'.

PLANT

Age of plant described: Approximately 10 years.

Vigor: This mango variety exhibits good vigor, including young trees.

Quantity of growth flushes per year: 100 to 150 cm good growth flushes per year depending on the year's weather.

Height and spread: 10 years old tree is approximately 3 meters tall and 3 meters wide.

Trunk circumference: Approximately 15 cm at the base.

Trunk color: Near RHS Greyed-Green 198A.

Trunk texture: Rough at the base, with bark ridged approximately 1 cm deep. Gradually becoming mainly smooth at upper trunk. Upper trunk with minor vertical ridges.

Branches:

*Branch diameter at the base*.—Approximately 8 to 12 cm.

*Branch length*.—Approximately 80 to 150 cm.

*Branch texture*.—Primary branches and scaffold branches mainly smooth.

*Branch color*.—Near RHS Grey 201A, 201B and 201C.

*Lenticels*.—Not observed.

FOLIAGE

Leaf:

*Arrangement*.—Alternate.

*Quantity per branch*.—Typically 50 to 80.

*Average leaf length*.—Average range 12-18 cm.

*Average leaf width*.—Average 5 cm.

*Shape*.—Oblanceolate.

*Leaf aspect*.—Slight downward curve.

*Base*.—Cuneate.

*Margin*.—Entire.

*Leaf internode length*.—Approximately 2 cm to 2.5 cm.

*Texture of top surface*.—Glabrous.

*Texture of bottom surface*.—Glabrous.

*Appearance of top surface*.—Matte.

*Appearance of bottom surface*.—Matte.

*Color*.—Young foliage upper side: Near RHS Yellow-Green 146C. Young foliage under side: Near RHS Green 137C. Mature foliage upper side: Near RHS Green 137A. Mature foliage under side: Near RHS Yellow-Green 146D.

Venation:

*Type*.—Pinnate.

*Venation coloration upper side*.—Near RHS Yellow-Green N144A.

*Venation coloration under side*.—Near RHS Yellow-Green 151A.

Petiole:

*Average length*.—Approximately 2 cm.

*Diameter*.—Approximately 0.6 cm.

*Color*.—Near RHS Yellow-Green 153A.

FLOWER

Inflorescence type and habit: Typical mango panicle/bunch.

*Number of fruit per inflorescence*.—Average range 1 to 4.

*Inflorescence length*.—25 cm.

*Inflorescence diameter at the widest point*.—13 cm.

*Inflorescence rachis color*.—Near RHS Greyed-Yellow 160B.

*Mean number of inflorescences per tree*.—90.

*Mean number of flowers per inflorescence*.—From five hundred to one thousand individual blossoms per inflorescence.

*Date of first full blooms*.—November until January in La Paz, Mexico.

Individual flowers:

*General*.—Individual blossoms are minute.

*Diameter of open flowers*.—When fully open, approximately 7 mm.

*Percent hermaphrodite flowers per inflorescence*.—Approximately 40%.

*Percent male flowers per inflorescence*.—Approximately 60%.

*Floral fertility*.—Normal, the subject tree is self-fertile.

Petals:

*Number of petals per flower*.—5.

*Length*.—0.1 mm.

*Diameter*.—0.05 mm.

*Petal texture*.—Slightly pubescent.

*Petal shape*.—Ovate.

*Petal color*.—Upper surface: Near RHS Yellow 11C. Lower surface: Near RHS Yellow 11C.

Sepals:

*Number of sepals per flower*.—5.

*Sepal size*.—About 0.5 mm wide and long.

*Sepal texture*.—Densely pubescent.

*Sepal shape*.—Ovate.

Rachis:

*Length*.—Average 12 cm.

*Diameter*.—Average 0.8 cm.

*Color*.—Near RHS Greyed-Orange 172D.

*Strength*.—Very strong.

REPRODUCTIVE ORGANS

Stamens: Shaped like small filaments.

*Stamen number in hermaphrodite flowers*.—5.

*Filament length*.—0.5 mm.

*Filament color*.—Near RHS Yellow-White 158C.

*Anther length*.—0.5 mm.

*Anther shape*.—Ovate.

*Anther color*.—Near RHS Yellow 10D.

*Pollen color*.—Near RHS Yellow 10A.

*Pollen production*.—Moderate.

Pistils:

*Pistil number*.—1 per flower.

*Pistil shape*.—Elliptic.

*Length*.—0.2 mm.

*Ovary number*.—Single.

*Diameter of ovary*.—0.5 mm.

*Ovary color*.—Near RHS Yellow 10D.

FRUIT

*Harvest time*.—Fruit mature.

*Average weight*.—400 to 700 grams.

*Average length*.—14 cm.

*Average width*.—10 cm.

*Stone description*.—Broad kidney shape, about 11 cm long and 1 cm.

*General fruit characteristics*.—Mature fruit elongated and yellow-orange in color with a rich red blush.

*Fruit yield*.—Approximately 80 fruit on an 18 year old tree, in a non-commercial setting.

*Shipping and keeping characteristics of fruit*.—Excellent shelf life of two to three weeks if cold storage of 50° F. is used.

Mature fruit:

*Shape*.—Broad kidney shape.

*Cross-sectional shape*.—Broad oval.

*Skin texture of mature fruit*.—Smooth.

*Main color*.—Near RHS Orange-Red 34C, speckles near Yellow 13B.

*Skin thickness*.—Approximately 1 mm.

*Adherence of flesh to skin*.—Moderate.

*Lenticel spotting*.—Dense.

*Fruit flesh texture*.—Very little fiber.

*Fruit flesh color*.—Near RHS Orange 25A.

OTHER CHARACTERISTICS

Disease resistance: This mango variety has shown very good resistance to fungal diseases. No other disease problems have been observed to affect this variety.

What is claimed is:

1. A new and distinct cultivar of *Mangifera* plant named 'Orange Star' as herein illustrated and described.

* * * * *